United States Patent [19]

Croudace et al.

[11] Patent Number: 4,701,274

[45] Date of Patent: Oct. 20, 1987

[54] TRISUBSTITUTED-BORATE COMPOUNDS

[75] Inventors: Michael C. Croudace, Huntington Beach; Leah T. Mendelson, Santa Ana; Richard A. Holstedt, Whittier, all of Calif.

[73] Assignee: Union Oil Company of California, Los Angeles, Calif.

[21] Appl. No.: 727,894

[22] Filed: Apr. 26, 1985

[51] Int. Cl.$^4$ .................. C10M 139/00; C10M 135/00
[52] U.S. Cl. .................. 252/46.3; 252/49.6; 568/6; 558/294
[58] Field of Search .................. 252/46.3, 49.6; 568/6; 558/294

[56] References Cited

U.S. PATENT DOCUMENTS

| | | |
|---|---|---|
| 2,975,134 | 3/1961 | Cook .................. 252/40.7 |
| 3,027,397 | 3/1962 | Steinberg et al. . |
| 3,074,885 | 1/1963 | Hunter et al. . |
| 3,221,035 | 11/1965 | Silver . |
| 3,347,793 | 10/1967 | Washburn et al. . |
| 3,356,707 | 12/1967 | Hinkamp et al. . |
| 3,359,298 | 12/1967 | Hunter et al. . |
| 3,509,054 | 4/1970 | Hinkamp et al. . |
| 4,115,286 | 9/1978 | Baldwin et al. . |
| 4,122,033 | 10/1978 | Black . |
| 4,400,284 | 8/1983 | Jessup et al. . |
| 4,410,436 | 10/1983 | Holstedt . |
| 4,412,928 | 11/1983 | Holstedt et al. . |
| 4,427,560 | 1/1984 | Holstedt et al. . |
| 4,465,605 | 8/1984 | Horodysky et al. . |
| 4,486,321 | 12/1984 | Horodysky et al. . |
| 4,486,322 | 12/1984 | Horodysky et al. . |
| 4,486,323 | 12/1984 | Horodysky et al. . |
| 4,490,265 | 12/1984 | Holstedt et al. . |
| 4,492,640 | 1/1985 | Horodysky et al. . |
| 4,511,516 | 4/1985 | Holstedt et al. . |
| 4,533,480 | 8/1985 | Holstedt et al. . |
| 4,547,302 | 10/1985 | Braid .................. 252/48.4 |

Primary Examiner—Jacqueline V. Howard
Attorney, Agent, or Firm—Dean Sandford; Gregory F. Wirzbicki; Michael C. Schiffer

[57] ABSTRACT

A lubricating composition having extreme pressure anti-wear properties comprises a lubricating oil and a trisubstituted-borate prepared by sulfurizing the reaction product of a boron compound, a phenol compound, and either a mono-functional compound or dihydroxy functional compound free of nitrogen.

42 Claims, No Drawings

TRISUBSTITUTED-BORATE COMPOUNDS

BACKGROUND OF THE INVENTION

The present invention relates to antiwear additives for lubricating compositions and specifically a trisubstituted-borate compound useful as a lubricating composition extreme pressure additive.

Lubricating compositions reduce friction and reduce or prevent destructive contact between moving metal surfaces as long as a film of the composition is maintained between the moving surfaces. This particular type of lubrication is referred to as hydrodynamic lubrication.

Some antiwear additives enhance a lubricating composition's hydrodynamic lubrication. However, when the pressure and/or rubbing speeds between the moving metal surfaces increase, the lubricating film is forced out from between the moving metal surfaces. This results in destructive metal-to-metal contact and wear. Lubrication under these extreme pressure conditions requires an additive that is adsorbed by or reacts with the metal to form an adherent protective film having a lower sheer strength than the metal. The type of lubrication needed under these conditions is called boundary lubrication with additives for this type of lubrication known as "extreme pressure antiwear additives."

Many extreme pressure antiwear additives are known, with the most commercially used additives being phosphorus containing compounds, such as dialkyl dithiophosphates. While these phosphorus-containing compounds provide a high degree of boundary lubrication, there is a move away from them, especially for use with internal combustion engines because of the belief that when these compounds are carried by the exhaust gases they react with and reduce the life of emission control catalysts.

Various types of boron-containing compounds are known as lubricating oil extreme pressure antiwear additives. One type of boron-containing compound antiwear additive is the ester of boron acids or oxides as disclosed in U.S. Pat. No. 2,975,134. Esters of dihydroxy compounds and boric acids or boron oxides are disclosed as useful antiwear additives. The major drawback with these types of compounds is their susceptibility to hydrolysis in the presence of water. Boron-containing compounds resistant to hydrolysis are disclosed in U.S. Pat. Nos. 3,509,054; 3,347,793; 3,359,298; and 3,356,707, wherein the compound is provided with at least one hindered phenol as the ester group. The use of 2-hydroxy-4-(mercaptohydrocarbyl)-1,3,2-dioxaborolanes and alkylammonium bis[(mercaptohydrocarbyl)ethylenedioxy]borates are disclosed as useful antiwear additives in lubricating compositions in U.S. Pat. No. 4,115,286.

While these boron-heterocyclic compounds provide boundary lubrication, they do not approach the boundary lubricating ability of phosphate-containing compositions. Thus there remains the need to find an extreme-pressure antiwear additive that can provide equivalent properties as, or superior properties to, phosphorus-containing compounds in lubricating compositions.

SUMMARY OF THE PRESENT INVENTION

The present invention resides in an extreme pressure antiwear additive which is the reaction product of a boron acid or oxide, at least one phenol compound, a mono- or polyhydroxy functional organic compound and sulfur or a sulfur compound to impart sulfur to the reaction product. The trisubstituted borate compound has the following general formula:

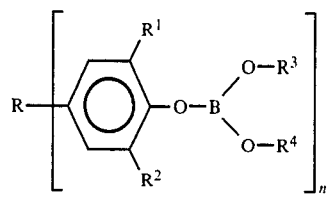

wherein: n is an integer; R is hydrogen or an organic radical; $R^1$, $R^2$, $R^3$, and $R^4$ are the same or different organic radical; and provided the trisubstituted-borate compound comprises sulfur. It is also suitable to provide that $R_3$ and $R_4$ are bonded together so as to form one radical attached to the boron through the oxygens.

The present invention further resides in a friction-reducing lubrication composition comprising a lubricating oil or grease and a sufficient amount of at least one trisubstituted borate compound of the invention.

DESCRIPTION OF THE PREFERRED EMBODIMENTS

The trisubstituted-borate compound of the present invention may be prepared from boron compounds, such as its acids including boriq acid, metaboric acid, the various polyboric acids, boronic acid, borinic acid, other equivalent acids, and the various oxides of boron and other equivalently reactive boron compounds, but preferably boron acids or oxides. The trisubstituted-borate compound is prepared by reacting the boron compound with at least one phenol compound and one or more other mono- or polyfunctional hydroxy organic compounds. The mono- or polyfunctional hydroxy compounds may be, saturated or unsaturated, aliphatic, alicyclic, or aromatic compounds, which for the purpose of the present invention, may possess heteroatoms, such as nitrogen or sulfur. The trisubstituted-borate compound is provided with sulfur, preferably a sulfide, by the method to be discussed below. The preferred hydroxy functional organic compounds are the mono-functional species.

In one embodiment of this invention where preferably only monohydroxy compounds are reacted with the boron compound, the trisubstituted-borate compound of the present invention is represented by the following general formula:

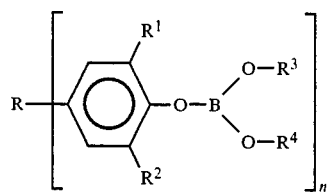

wherein:

n is an integer, preferably 1 to 3;

R is hydrogen or an organic radical, usually a $C_1$ to $C_{50}$ organic radical, preferably an organic radical derived from a $C_1$ to $C_{22}$ aliphatic, alicyclic or aromatic compound, more preferably an unsubstituted or substituted $C_1$ to $C_{22}$ alkyl, aryl, aralkyl, alkyloxy, aryloxy, aralkyloxy, alkenyl, alkynyl, alkenyloxy, alkynyloxy, aralkenyl, aralkynyl cycloalkenyl, cycloalkynyl, or cycloalkyl radical;

$R^1$ and $R^2$ are the same or different and are hydrogen or an organic radical, usually a $C_1$ to $C_{50}$ organic radical, preferably an organic radical derived from a $C_1$ to $C_{22}$ aliphatic, alicyclic or aromatic compound, more preferably an unsubstituted or substituted alkyl, aryl, aralkyl, alkyloxy, aryloxy, aralkyloxy, alkenyl, alkynyl, alkenyloxy, alkynyloxy, aralkenyl, aralkynyl, cycloalkenyl, cycloalkynyl or cycloalkyl radical having from 1 to 22 carbon atoms;

$R^3$, and $R^4$ are the same or different organic radical, usually a $C_1$ to $C_{50}$ organic radical, preferably an organic radical derived from a $C_1$ to $C_{22}$ aliphatic, alicyclic or aromatic compound, more preferably an unsubstituted or substituted alkyl, aryl, aralkyl, alkyloxy, aryloxy, aralkyloxy, alkenyl, alkynyl, alkenyloxy, alkynyloxy, aralkenyl, aralkynyl, cycloalkenyl, cycloalkynyl or cycloalkyl radical having from 1 to 22 carbon atoms;

and provided the compound comprises sulfur.

By "comprises sulfur" it is meant that the trisubstituted-borate compound possesses sulfur, which is bonded to or associated with the borate compound. The sulfur may be bonded or associated with the phenol group, the hydroxyl-functional groups or even the boron. Preferably the sulfur is covalently bonded to the borate compound as part of a sulfur group, preferably a sulfide group, which is bonded: (1) as an end group or as part of the compound backbone, as represented by thio—groups (—SH) and (—CH$_2$—S—CH$_2$), respectively; (2) as pendant from the compound, as represented by an episulfide group

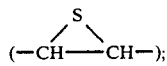

or (3) as a sulfide or polysulfide bridge (—S— or —S$_x$—, wherein x is 2 or more) between two organic radicals of the same or two different trisubstituted-borate compound(s) of this invention. It should be noted that the sulfur, particularly the sulfide bridges, may cross-link two or more trisubstituted-borate compounds of the present invention resulting in a dimer, oligomer or polymer of these trisubstituted-borate compounds.

In a preferred embodiment the phenol or other hydroxy functional compound is reacted with more than one boron compound, and it thus becomes a common organic group of more than one trisubstituted-borate compound of the invention. Preferably this common organic group is a substituent of the phenol compound which is represented in the above formula as the R radical and possesses a valency greater than one and preferably 2 or 3. Preferably the R radical is an alkdiyl or ardiyl radical and more preferably a radical of the formulae:

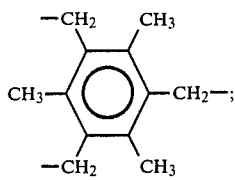

—(CH$_2$)$_2$—CO—O—(CH$_2$)$_x$—O—CO—(CH$_2$)$_2$—; or

—(CH$_2$)$_2$—CO—O—(CH$_2$)$_2$—S—(CH$_2$)$_2$—O—CO—(CH$_2$)$_2$— wherein X is an integer from 1 to 20. These common organic groups or R radicals result from compounds possessing two or more phenoxy substituents capable of reacting with boron compounds.

The reaction sequence of preparing boronheterocyclic compounds of the invention involve reacting a boron compound or mixture thereof either with: (1) the desired phenol or mixture of phenol compounds and then subsequently reacting this product with the other desired hydroxy-functional compound or compounds; or (2) the desired hydroxy-functional compound or compounds and then subsequently reacting this product with the phenol or mixture of phenol compounds. Preferably, the boron compound is first reacted with the phenol compound or compounds, and more preferably reacted at a 1:1 molar ratio. This facilitates the preparation of a phenol borate which is then further reacted with the hydroxy functional compound or compounds.

It may also be suitable when using a di-hydroxy-functional compound, such as a glycol, to react this compound first with the boron compound, preferably reacting at a 1:1 molar ratio, and then reacting this reaction product with the phenol compound.

Phenol compounds useful for preparing the trisubstituted-borate compound of the invention include 4-methyl-phenol; 2,2-ethylidene bisphenol; 1,3,5-trimethyl phenol; 4-ethoxyphenol; 2-mercaptophenol; and 3-mercaptophenol. Suitable mono-hydroxyl functional compounds include allyl alcohol; 3-butene-1-ol; 3-butene-2-ol; crotyl alcohol; cyclohexenol; pentenol; hexenol; heptenol; 2-methyl-3-butene-2-ol; octenol; nonenol; decenol; tallow alcohol; and oleyl alcohol and di-hydroxyl functional compounds are 2,3-dimethyl-2,3-butanediol, 1,2-ethanediol and 1,3-propanediol.

The reaction is typically carried out in a suitable solvent, e.g., toluene, dialkyl ether, benzene, xylene, or other solvents which are unreactive with the boron and hydroxy-functional compounds. The solvent is typically removed after the reaction is completed by vacuum distillation. Suitable temperatures for conducting the reaction is from about 80° C. to about 150° C. The completion of the reaction may be determined by comparing the measured amount of water or other reaction condensate produced by the reaction with the theoretical yield.

It is further preferable to acid catalyze the reaction using a suitable acid catalyst, such as p-toluene sulfuric acid, acetic acid, or other strong organic soluble acid. Typically, from about 0.05 mole percent to about 5.0 mole percent, based upon the moles of the boron compound being reacted, of the acid catalyst is used to conduct the reaction.

The trisubstituted-borate compound may be provided with sulfur by any known method. Preferably, either the phenol, other hydroxy-functional compound or both are provided with active allylic or benzylic hydrogen, such that in the above formulae at least one of the R, $R^1$, $R^2$, $R^3$, or $R^4$ radicals and more preferably at least one of the R, $R^3$, or $R^4$ radicals, is provided with at least one active allylic or benzylic hydrogen. Preferably at least one of R, $R^1$, $R^2$, $R^3$, or $R^4$, and more preferably R, $R^3$, or $R^4$, are an alkenyl, alkynyl, aralkenyl, cycloalkenyl, aralkynyl, cycloalkynyl, alkynyloxy, alkenyloxy, or aralkenyloxy radical with at least one unsaturation, and more, preferably an alkenyl or aryalkenyl radical. It is also preferable to provide hydrogens that are activated by the presence of a heteroatom contained by the phenol and/or other hydroxyfunctional compound. The boron-heterocyclic compound possessing the active hydrogen, either due to the presence of a heteroatom or allylic or benzylic unsaturation, is reacted with sulfur or a sulfur-containing compound, preferably by a free-radical initiation reaction process. Suitable sulfur containing compounds are sulfide compounds, e.g., dialkyldisulfide, alkynylthiol, or thio-acids. Free-radical initiators useful for preparing the sulfur-containing trisubstituted-borate compounds of the present invention are the various peroxide compounds, such as hydrogen peroxide, dialkyl hydroperoxide, dialkyl peroxide and persulfate compounds.

Other methods of providing the trisubstituted-borate compounds with sulfur may involve reacting unsaturated alcohols with sulfur prior to the reaction with the boron compound or reacting other thiohydroxy compounds with the boron compound.

Preferably, the trisubstituted-borate compound is provided with at least one sulfur group, preferably a sulfide group, and more preferably from 0.1 to about 2.0 equivalents of sulfide groups per trisubstituted-borate compound.

In one preferred embodiment of the present invention the boron-oxygen locus of the trisubstitutedborate compound is structurally hindered to inhibit hydrolytic attack of the boron-oxygen bonds. This structural hindrance is furnished by providing that the $R^1$ and $R^2$ radicals of the above formula are hindering groups. By "hindering group" it is meant a substituent that either is or is part of the particular organic radical that provides steric hindrance inhibiting the hydrolytic attack of the boron-oxygen bond of the trisubstituted-borate compound. Preferably $R^1$ or $R^2$ are the hindering groups and more preferably are the same or different tertiary alkyl, aryl, aralkyl, aryloxy, aralkyloxy, tertiary alkyloxy radical, still more preferably, the same or different tertiary alkyl radical. These preferred hindering groups are provided by reacting the boron compound with a hindered phenol, such as 2,6-di-t-butyl phenol; 4-methyl-2,6-di-t-butyl phenol; 2,2-ethylidene bis(4,6-di-t-butyl phenol); 1,3,5-trimethyl-2,4,6-tris (3,5-di-t-butyl-4-hydroxy benzyl) benzene; thiodiethylene bis(3,5-di-t-butyl-4-hydroxy hydrocinnamate); 1,6-hexamethylene bis(3,5-di-t-butyl-4-hydroxyhydrocinnamate) or 2,6-di-t-butyl-2-dimethylamino-p-cresol.

In another embodiment of this invention, the trisubstituted-borate compound is the reaction product of a phenol, preferably a hindered phenol, a di- or polyhydroxyl functional compound and a boron compound. Preferably, the di- or poly-hydroxy functional compound reacted is an organic compound free of nitrogen. Suitable dihydroxy compounds include 2,2-diethyl propane-1,3-diol; 2,3-dimethyl butanediol-2,3; 2-methyl pentane-1,3-diol; 2-methylpentadiol-2,4; 2-ethylhexane-1,3-diol; 2-ethyl 2-butyl propane-1,3-diol; and the various other known diols. This compound is represented by the following general formula:

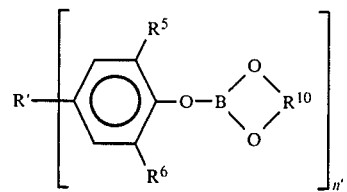

wherein n', R', $R^5$, and $R^6$ are as described above for n, R, $R^5$ and $R^6$, respectively, with being a di-valent organic radical, preferably an alkdiyl, ardiyl, alkdiyloxy, alkendiyl, alkyndiyl, or aralkdiyl radical having from 1 to 30 carbon atoms, more preferably an alkdiyl or ardiyl radical. Typically, is free of nitrogen.

Lubricating compositions which may contain the trisubstituted-borate compounds of the invention include substantially all oleaginous materials such as lubricating compositions comprising mineral or synthetic oil, or mixtures thereof, or a grease therefrom. Mineral oils may be of the naphthenic or paraffinic types with mineral and synthetic oils of any suitable lubricating viscosity range useful for the purposes of the present invention. In the case of greases, substantially any metal soap grease is improved with respect to antiwear properties and those greases which do not exhibit extreme pressure characteristics are improved in this respect by the use of the sulfur- containing trisubstituted-borate compounds of the present invention. The preferred oleaginous materials are lubricating oils suitable for use in gasoline powered internal combustion engines.

The trisubstituted-borate compound of the invention is incorporated into a lubricating oil or the like by blending or mixing therein a sufficient amount so as to provide the resultant lubricating composition with antiwear properties as determined by methods known to those known skilled in the art, such as by the Falex Method (ASTM D2670-67 (reapproved 1977). Preferably, the lubricating composition is provided with at least about 0.5 weight percent of the trisubstituted-borate compound of the invention, and more preferably from about 0.5 to about 15 weight percent of the trisubstituted-borate compound of the invention.

In another embodiment of the invention, copper corrosion in automotive engine bearings is inhibited by adding to the lubrication composition containing the trisubstituted compounds of the invention a corrosion inhibiting amount, normally from 0.001 to about 5 weight percent, preferably from 0.005 to about 2.5 weight percent based upon the weight of the total composition, of a hydrocarbon polysulfide derivative of 2,5-dimercapto-1,3,4-thiadiazole having the formula:

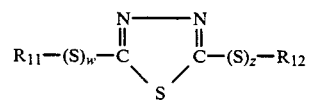

wherein $R_{11}$ and $R_{12}$ are the same or different moieties selected from hydrogen or straight or branched chain alkyl, cyclic or alicyclic alkyl, aryl or aralkyl radicals having from 2 to about 30 carbon atoms, and w and z are integers from 1 to 8. It should be noted that $R_{11}$ and $R_{12}$ cannot both be hydrogen because the compound would be rendered insoluble in lubricating oils. Thus, when $R_{11}$ is hydrogen, $R_{12}$ must be selected from one of the other moieties described above, and vice versa.

Suitable among such compounds are polysulfides of 1,3,4-thiadiazole-2,5-bis(alkyl, di, tri or tetra sulfide) containing from 2 to about 30 carbon atoms. Desirable polysulfides include 1,3,4-thiadiazole-2,5- bis (octyldisulfide); 1,3,4-thiadiazole-2,5-bis(octyl-trisulfide); 1,3,4-thiadiazole-2,5-bis(octyltetrasulfide); 1,3,4-thiadiazole-2,5-bis(dodecyldisulfide); 1,3,4-thia-diazole-2,5-bis(-dodecyltrisulfide); 1,3,4-thiadiazole-2,5-bis(dodecytetrasulfide; 2-lauryldithio-5-thioalpha-methyl-styryl-1,3,4-thiadiazole; 2 lauryltrithio-5-thioalpha-methylstyryl-1,3,4-thiadiazole; and 2-mercapto-5-octyldithio-1,3,4-thiadiazole and mixtures thereof.

A lead corrosion inhibiting amount of terephthalic acid may also be added to the lubricating composition. Generally, the terephthalic acid is incorporated into the lubricating composition at a concentration of from about 0.001 to about 1 weight percent, preferably from about 0.005 to about 0.05 weight percent based upon the weight of the total composition.

An oxidation inhibitor may also be employed in lubricating composition with the desired trisubstituted borate compound or in conjunction with the trisubstitued borate compound and other lead and copper corrosion inhibitors. Oxidation inhibitors are typically added to automotive engine lubricating oils and the like to prevent oxidative deterioration of organic materials. Any oxidation inhibitor known in the art may be employed, with suitable oxidation inhibitors being selected from the group consisting of bis(dithiobenzil) metal derivatives; sulfur bridged, bis(hindered phenols); and alkyl or diakyl, diphenylamines, dithiocarbamates and mixtures thereof. These compounds effectively limit or prevent the attack of oxidants on copper/lead metal. In addition, these compounds also help to control oil oxidation as manifested by reduced sludge and varnish formation, and by reduced oil thickening. The anti-oxidants are incorporated into lubricating compositions at oxidation inhibiting amounts usually at concentrations of from 0.01 to about 2 weight percent, preferably 0.01 to about 1.0 weight percent, more preferably from 0.025 to about 0.10 weight percent, based upon the weight of the total composition.

In still another embodiment it has been found that the presence of oil-soluble copper compounds, dissolved in an automotive engine oil with the trisubstituted borate compounds of the invention, provide enhanced anti-wear properties. In this embodiment of the invention less of the trisubstituted-borate compound of the invention may be used to obtain the same level of desired anti-wear protection. The preferred oil-soluble copper compounds are the copper carboxylates, such as copper naphthenate, with preferred concentrations of about 100 to 125 wppm as Cu. However, even higher concentrations may be used, for example, up to about 3 percent by weight if desired. An additional advantage in using copper carboxylates, such as copper naphthenate, is that they provide anti-oxidant properties. Other copper compounds also function in this manner, e.g., copper oleate. In U.S. Pat. No. 4,122,033, herein incorporated by reference in its entirety, lubricating compositions are taught employing copper compounds as anti-oxidants. Thus, the use of copper compounds having anti-oxidant properties functions in two ways in lubricating compositions, first, as an anti-oxidant and, second, for enhancement of the anti-wear properties of the sulfur-containing trisubstituted-borate compound of the invention.

In addition to providing enhanced anti-wear properties, it has also been found that a lubricating composition comprising a trisubstituted-borate compound of the invention, with an oil-soluble copper compound, exhibits anti-oxidant properties better than expected in comparison to the anti-oxidant properties of a lubricating composition comprising either the trisubstituted-borate or copper compound alone.

The following examples serve to further illustrate and instruct one skilled in the art in the best mode of practicing this invention and is not intended to be construed as limiting thereof.

EXAMPLE 1

To a round-bottom flask, equipped with a Dean-Stark apparatus, 11.45 g. of boric acid (0.185 moles), 40 g. crotyl alcohol (0.556 moles) and 100 ml toluene were added and heated to reflux. Water was azotropically distilled and collected in a Dean-Stark apparatus until 10 ml of water was collected, at which time it was believed the reaction was complete since the theoretically yield of water was approximately 10 ml from this reaction. At this point 40.7 g. of 4-methyl-1,6-di-t-butylphenol (0.185 moles) was added to the mixture. A distillation apparatus was then connected to the flask and the toluene and crotyl alcohol were distilled from the mixture. When no further crotyl alcohol could be distilled from the mixture, the reaction was believed complete. The recovered product was a greenish clear liquid which weighed 68.9 g. and was believed to be a 100% yield of (4-methyl-2,6-di-t-butylphenoxy)dicrotoxyborane.

This reaction product was then reacted with sulfur by adding 10 g. of the product to 1.72 g of sulfur (0.0536 moles) in a round-bottomed flask equipped with a reflux condenser. The mixture was heated to 175° C. and stirred for 1.5 hrs. Air was blown across the surface of the mixture for 2 hrs., after which the mixture was allowed to cool to room temperature. A brown, viscous, sticky product was retrieved.

EXAMPLES 2-5

Trisubstituted-borates in accordance with this invention were prepared by reacting (4-methyl-2,6-di-t-butylphenoxy)dicrotoxyborane with sulfur, following the procedure set forth in Example 1 above for reacting the reaction product with sulfur, with the amounts of (4-methyl-2,6-di-t-butylphenoxy)dicrotoxyborane and sulfur used in preparing each of Examples 2-5 listed below in Table I.

TABLE 1

| Example | (4-methyl-2,6-di-t-butylphenoxy) dicrotoxyborane | Sulfur |
| --- | --- | --- |
| 2 | 10 g (0.0266 moles) | 0.43 g (0.0134 moles) |
| 3 | 10 g (0.0266 moles) | 0.86 g (0.0269 moles) |
| 4 | 10 g (0.0266 moles) | 1.72 (0.0537 moles) |
| 5 | 15 g (0.0404 moles) | 3.60 g (0.1125 moles) |

EXAMPLES 6-11

Lubricating oil compositions were prepared using each of trisubstituted-borate compounds prepared above in Examples 1-5, by blending 2-weight percent of the composition of the particular borate into M6100 oil at a temperature of between 130° F. and 200° F. M6100 oil is a fully formulated motor oil containing zinc dialkyldithiophosphate in a concentration corresponding to 0.05 wt. % phosphorus. Each of the prepared lubricating compositions were analyzed for wear protection characteristics using the Falex Test Method D 2670-67 (reapproved 1977). The lubricating compositions were tested, along with a blank M6100 oil composition, under various Jaw Pound loads, with the results of the testing given below in Table 2, for each example as torque in pound-inches. As seen from the Falex testing results, lubricating compositions containing the borate compounds of this invention tolerate higher Jaw loads prior to seizure than did the blank composition, Example 11. The higher the load a composition withstands demonstrates better wear protection of that composition.

TABLE 2

| Ex. | Additive Ex. No. | Jaw Load (Pounds) | | | | | | | | | |
|---|---|---|---|---|---|---|---|---|---|---|---|
| | | 300 | 500 | 750 | 1000 | 1250 | 1500 | 1750 | 2000 | 2250 | 2500 |
| 6 | 1 | 3 | 5 | 10 | 15 | 20 | xx | | | | |
| 7 | 2 | 11.5 | 15 | 19 | 23 | 29 | xx | | | | |
| 8 | 3 | 11.5 | 15 | 18 | 21 | 28 | 34 | xx | | | |
| 9 | 4 | 12 | 16 | 20 | 24 | 29 | 35 | 45 | xx | | |
| 10 | 5 | 3 | 5 | 10 | 14 | 17 | 22 | 32 | 33 | 32 | xx |
| 11 | No Add. | 9 | 14 | 20 | xx | | | | | | |

EXAMPLE 12

To a round-bottomed flask, equipped with a Dean Stark apparatus, 66 grams of 4-methyl-di-t-butylphenol (0.3 moles), 43.2 grams crotyl alcohol (0.6 moles), 18.3 grams boric acid (0.3 moles), 2 grams p-toluene sulfonic acid (0.01 moles) and 375 millimeters of xylene were added. The mixture was then heated to reflux, co-distilling off both water and xylene through the Dean Stark apparatus. When no more water could be distilled off, approximately after the removal of 22.2 milliliters of water, it was believed that the reaction had been completed, based upon the theoretical yield of water resulting from the condensation reaction of the butylphenol, crotyl alcohol, and boric acid. The remaining xylene was then vacuum distilled off leaving a product having a yield of approximately 70.69 grams, which was believed to be a 4-methyl-di-t-butylphenol/crotyl alcohol borate comprised of 2 moles of crotyl alcohol and 1 mole of 4-methyl-di-t-butylphenol reacted with the boric acid.

The above reaction product was then sulfurized by placing 50 grams of the reaction product, 2.15 grams sulfur and 150 milliliters of xylene into a round-bottom flask and refluxing this mixture for four hours. The xylene was then vacuum distilled off leaving a product yield of 44.28 grams.

EXAMPLE 13

A trisubstituted borate compound in accordance with this invention was prepared from 4-methyl-di-t-butylphenol, tallow alcohol and boric acid using the procedures set forth above for Example 12, with the amount of each material as set forth below in Table 3. This reaction product was then sulfurized by the procedure set forth above in Example 12 with the amount of reaction product and sulfur used listed below in Table 4. The final amount of sulfurized reaction product obtained was 48.22 grams.

TABLE 3

| Ingredient | Amount |
|---|---|
| 4-methyl-di-t-butylphenol | 44 gms (0.2 moles) |
| Tallow alcohol | 104 gms (0.4 moles) |

TABLE 3-continued

| Ingredient | Amount |
|---|---|
| Boric acid | 12.4 gms (0.2 moles) |
| t-toluene sulfonic acid | 2 gms (0.01 moles) |
| Xylene | 450 moles |

TABLE 4

| Ingredient | Amount |
|---|---|
| Reaction product | 50 gms |
| Sulfur | 0.67 gms |

While the preferred embodiments have been described and illustrated, various modifications and substitutions may be made thereto without departing from the spirit and scope of this invention. Accordingly, it is to be understood that the present invention has been described by illustration and not limitation, and no limitations should be imposed other than as indicated in the following claims.

What is claimed is:

1. A reaction product of sulfur with an intermediate reaction product of a boron compound and one monofunctional phenol compound, and one or more monofunctional, aliphatic compounds, said phenol compound being reacted with said boron compound in a 1:1 molar ratio.

2. A reaction product of a boron compound, one phenol compound, and one aliphatic dihydroxyl-functional compound essentially free of nitrogen, wherein the reaction product is further reacted with sulfur in such a manner to provide that the product comprises sulfur, and wherein the phenol compound and the boron compound react in a 1:1 molar ratio.

3. The reaction product of claims 1 or 2 wherein the boron compound is a boric acid or oxide.

4. The reaction product of claim 3 wherein the phenol compound is a hindered phenol.

5. The reaction product of claim 3 wherein the phenol compound is 2,6-di-t-butyl phenol; 4-methyl-2,6-di-t-butyl phenol; or 2,6-di-t-butyl-2-dimethylamino-p-cresol.

6. The reaction product of claim 4 wherein the phenol compound possesses allylic or benzylic unsaturation.

7. A compound of the formula:

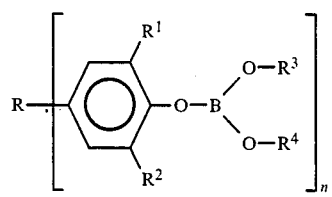

wherein n is an integer of at least one;
R is hydrogen or an organic radical;
$R^1$ and $R^2$ are the same or different and are hydrogen or a $C_1$ to $C_{50}$ organic radical;
$R^3$, and $R^4$ are the same or different monovalent organic radical; and
wherein the compound comprises sulfur.

8. A compound of the formula:

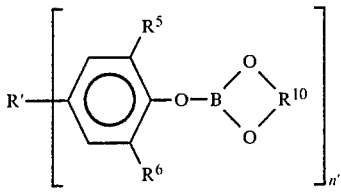

wherein:
n' is an integer of at least one;
R' is hydrogen or an aliphatic radical;
$R^5$ and $R^6$ are the same or different and are hydrogen or a $C_1$ to $C_{50}$ organic radical;
$R^{10}$ is a divalent aliphatic radical free of nitrogen; and wherein the compound comprises sulfur.

9. The compound of claim 7 wherein R, $R^1$, and $R^2$, are the same or different organic radical derived from a $C_1$ to $C_{22}$ aliphatic, or aromatic compound.

10. The compound of claim 7 wherein R, $R^1$, and $R^2$, are the same or different $C_1$ to $C_{22}$ alkyl, aryl, aralkyl, alkyloxy, aryloxy, aralkyloxy, alkenyl, alkynyl, alkenyloxy, alkynyloxy, aralkenyl, aralkynyl, cycloalkenyl, cycloalkynyl or cycloalkyl radical.

11. The compound of claim 8 wherein R', $R^5$ and $R^6$ are the same or different organic radical derived from a $C_1$ to $C_{30}$ alicyclic or aromatic compound.

12. The compound of claim 8 wherein R', $R^5$ and $R^6$ are the same or different $C_1$ to $C_{22}$ alkyl, aryl, aralkyl, alkyloxy, aryloxy, aralkyloxy, alkenyl, alkynyl, alkenyloxy, alkynyloxy, aralkenyl, aralkynyl, cycloalkenyl, cycloalkynyl or cycloalkyl radical.

13. The compound of claim 9 wherein $R^1$ and $R^2$ are the same or different tertiary alkyl, aryl, aralkyl, tertiary alkyloxy, aryloxy or aralkyloxy radical.

14. The compound of claim 10 wherein $R^1$ and $R^2$ are the same or different tertiary alkyl, aryl, aralkyl, tertiary alkyloxy, aryloxy or aralkyloxy radical.

15. The compound of claim 9 wherein $R^1$ and $R^2$ are the same or different tertiary alkyl radical.

16. The compound of claim 10 wherein $R^1$ and $R^2$ are the same or different tertiary alkyl radical.

17. The compound of claim 14 wherein R, $R^3$ and $R^4$ are the same or different alkenyl, alkynyl, cycloalkenyl, cycloalkynyl, alkynyloxy, or alkenyloxy.

18. The compound of claim 16 wherein R, $R^3$ and $R^4$ are the same or different alkenyl radical.

19. The compound of claim 12 wherein $R^5$ and $R^6$ are the same or different tertiary alkyl, aryl, aralkyl, tertiary alkyloxy, aryloxy or aralkyloxy radical.

20. The compound of claim 19 wherein $R^5$ and $R^6$ are the same or different tertiary alkyl radical.

21. The compound of claim 20 wherein $R^{10}$ is a $C_1$ to $C_{30}$ alkdiyl, alkdiyloxy, alkendiyl, or alkyndiyl radical.

22. The compound of claim 19 wherein $R^{10}$ is an alkdiyl radical.

23. The compound of claim 16, 17, or 18 wherein R is

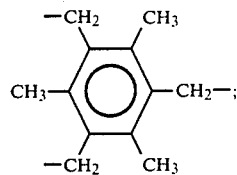

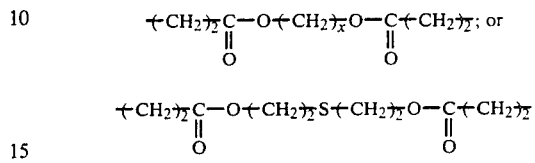

wherein x is an integer from 1 to 16.

24. The compound of claim 20 wherein $R^{10}$ is an alkdiyl radical.

25. A composition comprising: a lubrication oil or grease; and an anti-wear enhancing amount of the compound of claims 1, 2, 7, 8, 14, 18, 20 or 21.

26. The composition of claim 25 wherein said compound comprises from about 0.5 to about 15 weight percent of the composition.

27. The composition of claim 26 further comprising an oil-soluble copper compound.

28. A compound of the formula:

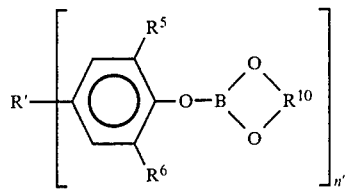

wherein:
n' is an integer of at least two
R' is hydrogen or an organic radical;
$R^5$ and $R^6$ are the same or different and are hydrogen or an organic radical;
$R^{10}$ is a divalent organic radical; and wherein the compound comprises sulfur.

29. The compound of claim 28 wherein R', $R^5$, and $R^6$ are the same or different organic radical derived from a $C_1$ to $C_{30}$ aliphatic, alicyclic, or aromatic compound.

30. The compound of claim 28 wherein R', $R^5$, and $R^6$ are the same or different $C_1$ to $C_{22}$ alkyl, aryl, aralkyl, alkyloxy, aryloxy, aralkyloxy, alkenyl, alkynyl, alkenyloxy, alkynyloxy, aralkenyl, aralkynyl, cycloalkenyl, cycloalkynyl, or cycloalkyl radical.

31. The compound of claim 30 wherein $R^5$ and $R^6$ are the same or different tertiary alkyl, aryl, aralkyl, tertiary alkyloxy, aryloxy, or aralkyloxy radical.

32. The compound of claim 30 wherein $R^5$ and $R^6$ are the same or different tertiary alkyl radical.

33. The compound of claim 31 wherein $R^{10}$ is a $C_1$ to $C_{30}$ alkdiyl, alkdiyloxy, alkendiyl, or alkyndiyl radical.

34. The compound of claim 31 wherein $R^{10}$ is an alkdiyl radical.

35. The compound of claim 32 wherein $R^{10}$ is an alkdiyl radical.

36. The compound of claim 12, 21, 24, 28 or 35 wherein R' is

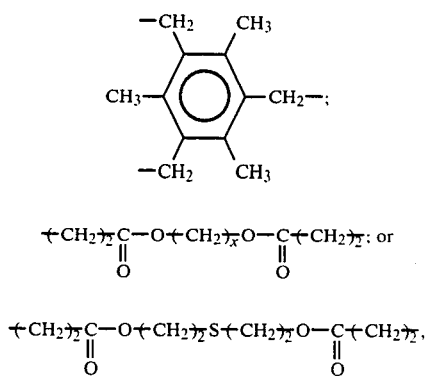

wherein x is an integer from 1 to 16.

37. A composition comprising a lubrication oil or grease, and an anti-wear enhancing amount of the compound of claim 28, 35 or 36.

38. The composition of claim 37 further comprising oil-soluble copper compound.

39. A composition comprising a lubrication oil or grease, and an anti-wear enhancing amount of the compound of claim 36.

40. A composition comprising a lubrication oil or grease and an anti-wear enhancing amount of the compound of claims 9, 10, 11, 13, 15 or 19.

41. A composition comprising a lubrication oil or grease, and an anti-wear enhancing amount of the compound of claim 23.

42. A composition comprising a lubrication oil or grease, and an anti-wear enhancing amount of the compound of claims 29, 31, 32 or 34.

* * * * *

UNITED STATES PATENT AND TRADEMARK OFFICE
CERTIFICATE OF CORRECTION

PATENT NO. : 4,701,274

DATED : October 20, 1987

INVENTOR(S) : Michael C. Croudace, Leah T. Mendelson, and Richard A. Holstedt

It is certified that error appears in the above-identified patent and that said Letters Patent is hereby corrected as shown below:

Column 11, line 5, delete the comma.

Column 11, lines 5 and 6, change "organic" to --aliphatic--.

Column 11, line 21, change "aliphatic" to --organic--.

Column 11, line 28, delete the comma.

Column 11, line 60, change "19" to --12--.

Column 11, line 63, change "20" to --19--.

Column 12, line 41, delete "hydrogen or".

Column 12, line 44, change "organic" to --aliphatic--.

Column 14, line 3, change "36" to --24--.

Signed and Sealed this

Third Day of May, 1988

Attest:

DONALD J. QUIGG

Attesting Officer

Commissioner of Patents and Trademarks